United States Patent [19]

Watson

[11] Patent Number: 5,053,006

[45] Date of Patent: Oct. 1, 1991

[54] METHOD FOR THE PERMANENT OCCLUSION OF ARTERIES

[76] Inventor: Brant D. Watson, 8405 NW. 8th St., No. 306, Miami, Fla. 33126

[21] Appl. No.: 503,130

[22] Filed: Apr. 2, 1990

Related U.S. Application Data

[63] Continuation of Ser. No. 183,046, Apr. 19, 1988, abandoned.

[51] Int. Cl.$^5$ ............................................. A61M 31/00
[52] U.S. Cl. ......................................... 604/52; 606/2; 128/395; 128/898
[58] Field of Search ....................... 604/20, 52, 49, 53, 604/21; 128/303.1, 664-666, 395, 398

[56] References Cited

U.S. PATENT DOCUMENTS

| | | | |
|---|---|---|---|
| 4,268,495 | 5/1981 | Muxfeldt et al. | 128/659 |
| 4,597,379 | 7/1986 | Kihn et al. | 128/303.1 |
| 4,637,815 | 1/1977 | Lemol | 604/49 |
| 4,672,969 | 6/1987 | Dew | 128/303.1 |
| 4,735,201 | 4/1988 | O'Reilly | 128/303.1 |
| 4,799,479 | 1/1989 | Spears | 128/303.1 |

OTHER PUBLICATIONS

Watson et al., *Ann. Neurol.*: 17:497-504, 1985. "Introduction of Reproducible Brain Information by Photochemically Initiated Thrombosis".

"Induction of Conjunctival Transdifferentiation on Vascularized Corneas by Photothrombatic Occulusion of Corneal Neovascularization"; Huang et al., *Opthamology*; 95:228-235, 1988.

"Amelioration of Experimental Lipid Keratopathy by Photochemically Induced Thrombosis of Feeder Vessels"; *Arch Opthamol*, Jul. 1977, vol. 105(7); pp. 983-988; Mendelson et al.

Watson et al.; "Argon Laser-Induced Arterial Photothrombosis"; *J. Neurosurg.*; ; May 1987, vol 66(5); pp. 748-754.

Wharen et al.; "The Nd:YAG-Laser in Neurosurgery"; *J. Neurosurg.*; 60:540-547, 1984.

Klaassen; "Pharmacokinetics of Rose Bengal in the Rat, Rabbit, Dog; and Guinea Pig"; *Toxicology and Applied Pharmacology*, 38:85-100, 1976.

Pirotte; "Study of $^{131}$I-Rose Bengal Kinetics in Normal Man: A Critical Evaluation of Three-Compartment Model"; *Biomedicine*, 32:17-21, 1980.

Ophthalmic Res. 13:139-150 (1981) Boergen et al., "Laser-Induced Endovascular Thrombosis as a Possibility of Selective Vessel Closure".

Abstract of Retina Paper Presentation, "Photochemical Vessel Closure in Normal Retina and Choroid via Laser-Activated Chloro-Aluminum Sulfonate Phthalocyanine", Grossmann et al. 8-5:30 p. 371; Laser Research Laboratory Mass. Eye and Ear Infirmary, Harvard Medical School; Boston, MA.

Abstract of Retina Paper Presentation, "Angiography and Photodynamic Therapy of Experimental Choroidal Neovascularization Using Phthalocyanine Dye"; Kiman et al., Laser Research Laboratory, Mass. Eye and Ear Infirmary, Harvard Medical School; Boston, MA.

Photochemistry and Photobiology; vol. 46 No. 1; pp. 103-108; 1987 Chopp et al. "Photodynamic Therapy of Normal Cerebral Tissue in the Cat: a Noninvasive Model for Cerebrovascular Thrombosis".

Tseng et al. "Photodynamic Therapy Induced Ultrastructural Alterations in Microvasculature of the Rat Cremaster Muscle" [School of Medicine, University of Louisville; Louisville, Ky. 40292].

Gastroenterology 1988:95:1258-1264; Nishioka et al., "Selective Vascular Coagulation of Rabbit Colon Using a Flashlamp-Excited Dye Laser Operating at 577 Nanometers".

Microvascular Research, vol. 28; 125-130 (1984) Gange et al., "Effect of Preirradiation Tissue Target Temperature Upon Selective Vascular Damage Induced by 577-nm Tunable Dye Laser Pulses".

Science, vol. 220, pp. 524-527; "Selective Photothermolysis: Precise Microsurgery by Selective Absorption of Pulsed Radiation".

Society for Neuroscience Abstracts, Nov. 1986 22.1; Watson et al. "Photochemical Induction of Arterial Thrombi and Their Dissociation by Recombinant Tissue Plasminogen Activator".

ARVO Abstracts Mar. 1987 #13; p. 222, Mendelsohn et al.; "Amelioration of Experimental Lipid Ceratopatry by Photochemically Induced Thrombosis of Feeder Vessels."

ARVO Abstracts, Mar. 1987 #24, ". . . Conjunctival Transdifferentiation by Photothrombosis with Rose Bengal and Argon Laser"; Huang et al.

Neurology 37 (Suppl. 1) Mar. 1987; p. 131 #5, Ginsberg et al. "Hyperglycemia Increases Infarct Size in Collaterally Perfused; but not End Arterial Vascular Territories: Results in Two Thrombotic Stroke Models".

American Society for Laser Medicine and Surgery Abstracts; Apr. 1987, p. 127, #258; Watson et al. "Rose Bengal-Induced Photosensitized Thrombosis of Arteries: Implications for Ophthalmic Photoradiation Therapy".

(List continued on next page.)

*Primary Examiner*—C. Fred Rosenbaum
*Assistant Examiner*—Kathleen A. Daley
*Attorney, Agent, or Firm*—Cushman, Darby & Cushman

[57] ABSTRACT

A new, non-mechanical method of inducing the complete occlusion of arteries is disclosed. Arteries are occluded thrombotically by means of a rose bengal dye-sensitized photochemical reaction initiated in non-thrombogenic vascular endothelium by light at a wavelength sufficient to electronically excite the rose bengal molecules. To blood platelets, the rose bengal-photosensitized endothelial surface becomes thrombogenic; accordingly, platelet adherence is followed by intense platelet aggregation resulting in complete occlusion of the artery.

23 Claims, No Drawings

OTHER PUBLICATIONS

American Society for Laser Medicine and Surgery Abstracts; Apr. 187; p. 119 #220, Huang et al., "Induction of Conjunctival Transdifferentiation by Photothrombosis with Rose Bengal and Argon Laser".

Circulation Research, vol. 40; No. 3, Mar. 1977; pp. 320–327, Rosenblum et al. "Platelet Aggregation in Cerebral Microcirculation: Effect of Aspirin and Other Agents".

J. Neurosurg. 66: 748–754; 1987, Watson et al. "Argon Laser-Induced Arterial Photothromboisis"; Characterization and Possible Application to Therapy of Arteriovenous Malformations.

*Cerebrovascular Diseases*, ed. Raichle et al.; Raven Press, N.Y. 1987 "Mitigation of Evolving Cortical Infarction in Rats by Recombinant Tissue Plasminogen Activator Following Photochemically Induced Thrombosis" by Watson et al., pp. 317–330.

Microvascular Research, 26; 238–249 (1983) Hermann et al. "Platelet Aggregation Induced in the Hamster Cheek Pouch by a Photochemical Process with Excited Fluorescein Isothiocyanate-Dextran". pp. 238–249.

Arch Ophthalmol—vol. 105; Aug. 1987, Nanda et al. "A New Method for Vascular Occlusion".

Arch Ophthalmol—vol. 105; Jul. 1987, Mendelsohn et al. "Amelioration of Experimental Lipid Keratopathy by Photochemically Induced Thrombosis of Feeder Vessels". pp. 983–988.

Ophthalmology, vol. 95, #2; Feb. 1988, pp. 228–235, Huang et al., "Induction of Conjunctival Transdifferentiation on Vascularized Cornea by Photothrombotic Occlusion of Corneal Neovascularization".

J. of Cerebral Blood Flow and Metabolism, 1988, Raven Press, Ltd. N.Y.; Nakayama et al. "Photothrombotic Occlusion of Rat Middle Cebral Artery; Histopathological and Hemodynamic Sequelae of Acute Recanalization".

Annals of Neurology, vol. 17; No. 5, May 1985; Watson et al., "Induction of Reproducible Brain Infarction by Photochemically Initiated Thrombosis".

Lasers in Medical Science vol. 1; 1986, Boulnois "Photophysical Processes in Recent Medical Laser Developments: A Review".

METHOD FOR THE PERMANENT OCCLUSION OF ARTERIES

This invention was made with Government support under the National Institutes of Health research grant No. 1 RO1 NS-23244. The Government has certain rights in this invention.

This is a continuation-in-part (CIP) continuation of application Ser. No. 07/183,046, filed Apr. 19, 1988, which was abandoned upon the filing hereof 07/503,130.

BACKGROUND OF THE INVENTION

1. Field of the Invention

The present invention relates to a method for inducing efficient and permanent clotting in arteries. More particularly, the present invention relates to the interaction of rose bengal dye (injected into the bloodstream) with light at a wavelength sufficient to electronically excite the rose bengal molecules to effect the complete occlusion of arteries.

2. Description of the Prior Art

Heretofore, the prior art has not disclosed a method for inducing efficient and permanent clotting in arteries.

Among the objects of the present invention is the provision of a rapid, as well as safe and effective, method of permanently occluding arteries. The foregoing as well as still further objects of the present invention will be more fully understood from the following description.

According to the present invention, by utilizing the principle of photothrombotic occlusion, permanent cessation of blood flow in arteries can be achieved without the need for (1) mechanical contact which may lead to hemorrhage and damage to adjacent tissue, or (2) the use of photocoagulation techniques which may lead to thermal injury of adjacent tissue.

The present method utilizes an intravascular photochemical reaction to induce structural damage to the vascular endothelium of the artery. The photochemical process is mediated by rose bengal, a fluorescein dye. The photothrombotic effect is believed to originate at the endothelial luminal surface of the artery where a portion of the rose bengal dye is readily absorbed following intravenous injection. The photochemical process is initiated by light at a wavelength sufficient to electronically excite the rose bengal molecules. A Type II photochemical process is begun in which the energy of excitation is transferred to molecular oxygen; this results in the efficient creation of singlet molecular oxygen, a metastable, highly reactive species.

Singlet oxygen initiates direct peroxidation of unsaturated fatty acids and proteins in the luminal surface, leading to structural damage which stimulates platelet adherence. Platelet adherence is followed by intense platelet aggregation, resulting in complete occlusion of the artery.

While other investigators have used sodium fluorescein as a photosensitizer in the photochemical occlusion of small blood vessels, the present inventor has found rose bengal to be a much more efficient photosensitizer. The efficiency of rose bengal is due to the quantum efficiency of singlet molecular oxygen production following quenching of the lowest dye triplet state by ground state oxygen molecules; this is 76% for rose bengal and barely 3% for sodium fluorescein.

Because the photochemical reaction of the present invention is mediated by electronic-state transitions in molecules, it does not depend on the generation of heat to exert its toxic effect on the artery being occluded. The present method thus avoids the following liabilities of the commonly attempted method of photocoagulation for occluding blood vessels:

(1) In arteries, it is generally not possible to coagulate blood or to damage endothelium by heat-induced protein denaturation alone. The local cooling effect of the high blood flow rate is sufficient to inhibit this type of damage.

(2) The incident laser intensities employed during attempts to photocoagulate blood vessels can destroy the blood vessel wall and induce hemorrhage, as well as damage surrounding tissue unnecessarily. In contrast, the presently disclosed photochemical method facilitates occlusion at much lower intensities. Thus, although heat is generated locally during formation of a photochemically induced thrombus, no damage to the adventitia (outer wall of the blood vessel) is seen, and damage to surrounding tissue is minimal.

(3) In small blood vessels (i.e., blood vessels with a diameter of less than about 200 $\mu$m) in which occlusion by photocoagulation is difficult but possible with deleteriously high incident intensities, it is well known that recanalization can occur spontaneously within a few weeks.

Rose bengal (disodium tetraiodo-tetrachloro-fluorescein) is believed to be quite safe when intravenously administered to humans in doses sufficient to permit photothrombotic occlusion of arteries. A blood concentration of 680 $\mu$M used in rats in experimental work performed by the present inventor is only four times the usual concentration of sodium fluorescein commonly used in human retinal angiography. Other work in which new corneal blood vessels in rabbits were occluded by the present technique required as little as 136 $\mu$M of rose bengal dye. On a molar basis, the $LD_{50}$'s (the median doses which will kill within a stated period of time 50 percent of the animals inoculated) observed in mice for the compounds erythrosin B (disodium tetraiodofluorescein), eosin Y (disodium tetrabromofluorescein) and phloxine B (disodium tetrabromo-tetrachlorofluorescein) are approximately 0.8, 0.8 and 0.4 mM/kg, respectively. As it may be assumed that the effect of adding four chlorine atoms decreases the $LD_{50}$ for rose bengal dye to half that for erythrosin B (as it does for phloxine B compared to eosin Y), then the $LD_{50}$ for rose bengal dye is also 0.4 mM/kg, or 4.6 mM in blood.

Rose bengal dye has been used by the present inventor in a photochemical reaction to induce photothrombotic stroke in rats (Watson et al., *Ann. Neurol.*, 17:497–504, 1985). The blood vessels that were occluded, however, were not arteries, but were small vessels such as arterioles, venules and capillaries and much work had to be done to adapt the original technique to occlude the larger diameter, faster flowing arteries.

The photochemical reaction is expected to be particularly useful in clinical situations which require the stoppage of blood flow in arteries by non-mechanical means. This feature is especially useful when the arteries are very fragile as, for example, in the case of the thin-walled, high flow feeder vessels on the underside of the nidus of an arteriovenous malformation (AVM) of the nervous system.

Although photocoagulation of the AVM nidus and/or of its perforating vessels with argon or neodymium-:yttrium-aluminum-garnet (Nd:YAG) lasers has been undertaken, this method has not been found to be effective. For example, Whalen et al. (*J. Neurosurg.*, 60:540-547, 1984) does not observe . consistent occlusion of the shunt vessels despite administration of total doses in the kilojoule range to various AVM's; insufficient heat absorption by the lesion owing to its high rate of blood flow evidently impedes photocoagulation.

Because the photochemical reaction of the present invention is mediated by electronic-state transitions, the process of photothrombosis, unlike photocoagulation, can be initiated in blood vessels with high flow rates without the requirement of increased temperature. Accordingly, permanent cessation of flow in, for example, the feeding vessels of an AVM, as well as other thin-walled, high flow vessels, can be achieved without the need for mechanical contact or induction of thermal injury.

Another important area of use of the presently disclosed photothrombotic method is in ophthalmic surgery, where occlusion of undesirable arteries is a common problem. Indeed, it is likely that the most immediate clinical application of the rose bengal-mediated photothrombotic method is the occlusion of abnormally growing blood vessels in the eye.

In the case of neovasculature (new vessel growth) of the cornea, induced, for example, by denuding injury such as by chemical burns, contact lens-induced lipid keratopathy or corneal graft rejection, the photothrombotic technique is very effective in inducing permanent occlusion of the network of new blood vessels and thereby inducing conjunctival transdifferentiation (transformation into cornea-like morphology) on vascularized corneas. When the photothrombotic method is used, no heat-induced inflammatory response is noted, as has occurred in attempts to occlude corneal neovasculature by photocoagulation (using an argon ion laser alone to damage vessels by absorbed heat, not by photochemistry). This is because the chief effect of the rose bengal is to greatly lower the light intensity required to induce occlusion, in this case, specifically by blood platelets in these small vessels, following activation of the rose bengal by, for example, a low-intensity argon ion laser beam and the resultant platelet response to the photochemically damaged endothelium. Similar considerations may apply in the case of retinal neovasculature, such as occurs in diabetic retinopathy.

The photochemical interaction between intravenously injected rose bengal dye and light at a wavelength sufficient to electronically excite the rose bengal molecules can be used to initiate permanent thrombotic occlusion in the corneal neovasculature of rabbit eyes with experimentally induced lipid keratopathy. The photothrombotic procedure does not produce corneal edema or polymorphonuclear leukocyte infiltration, as has been found in studies employing laser-induced photocoagulation. Thus, the formation of additional neovascularization and lipid deposition, which takes place with photocoagulation, is avoided.

Potential uses for the photothrombotic method include injuring cells other than vascular endothelium, for example, tumor cells, e.g., highly vascularized skin tumors or in Greene's ocular melanoma. Occlusion of the feeding vessels would facilitate ischemic necrosis and consequent sloughing away of the tumor mass. This would be much preferred to surgery, in which case a large wound area is created. Another difficult problem is internal bleeding from the liver, which is difficult to stanch surgically. The presently disclosed photochemical method could be used to seal the bleeding blood vessel ends thrombotically by areal irradiation, without introducing the complications of thermal injury to functioning tissue.

As an extension of the principle of photochemically induced damage to endothelium, a photosensitizing dye could be attached to an isothiocyanate group, which itself can be complexed to a monoclonal antibody. This would make possible the localization of damage to specific molecular sites in a membrane.

Owing to steric hindrance, rose bengal cannot bind to an isothiocyanate group. However, the closely related dye, erythrosin B (mentioned above), can bind to isothiocyanate, and the resultant compound is commercially available.

The present inventor has attached erythrosin B to an endothelial antibody. Erythrosin B alone has been administered intravenously by the inventor to photothrombotically occlude the rat middle cerebral artery in the same fashion as rose bengal.

SUMMARY OF THE INVENTION

The present invention is directed to a method of inducing the permanent occlusion of arteries. According to this method, the absorption by systemically injected rose bengal dye of light at a wavelength sufficient to electronically excite the rose bengal molecules initiates singlet-oxygen motivated photochemical injury to the vascular endothelium. These luminal alterations stimulate intense platelet adherence and physiological aggregation, which leads to total occlusion of the artery at the point of interaction of the rose bengal dye and the light beam, which is preferably a laser light beam.

DETAILED DESCRIPTION OF THE INVENTION

The present invention is directed to a method for inducing the complete occlusion of arteries. The method utilizes an intravascular photochemical reaction to induce structural damage to normally non-thrombogenic vascular endothelium. The photochemical process is mediated by rose bengal, a potent photosensitizing dye injected into the bloodstream. Absorption by the injected rose bengal dye of light at a wavelength sufficient to electronically excite the rose bengal molecules induces photochemical injury via singlet oxygen peroxidation reactions in the vascular endothelium at the point of interaction of the rose bengal and the light beam, which is preferably a laser light beam.

Because wavelengths in the range of 510 nm to 580 nm are readily absorbed by rose bengal, and laser beams, for example, are easily focused, the rose bengal-sensitized photochemical reaction can be made sufficiently intense to stimulate platelet adhesion and aggregation even in high-flow vessels. In large arteries, the thrombus is a mixed aggregate of platelets, red blood cells and coagulum in the irradiated arterial segment; distally the thrombus consists of coagulated red blood cells. In small arteries, the thrombus is almost entirely composed of platelets.

A laser light beam is a particularly advantageous source of light as it can be directed and focused precisely, with sufficient intensity to overcome the dilution effect of the flowing blood, and yet it acts fast enough so as to minimize damage to adjacent structures. For example, at energy fluences (energy deposited per unit area) of 35 kJ/sq cm for large arteries and 3.5 kJ/sq cm for small arteries, occlusion occurs within 3 minutes or less. No damage to the adventitia or surrounding tissue can be observed during or following irradiation of the artery except that vasa vasorum, if present, is most likely occluded.

Examples of lasers that can be used to provide the light beam include the He-Ne laser, the argon ion laser and the argon-pumped dye laser. The 543.5 nm He-Ne laser, for example, can excite rose bengal with an efficiency of 58% of the maximum. (The wavelength at which excitation efficiency for rose bengal is maximal in tissue occurs at 562 nm.) Because the maximum theoretical power output is only 4 or 5 milliwatts, the 543.5 nm He-Ne laser is not used in clinical applications at this time. However, this laser is expected to be particularly useful in permanently occluding relatively low-flow arteries, smaller than about 200 $\mu$m, such as those in the choroid of the eye.

The argon ion laser is the most common clinical laser used at this time. Although the commonly used argon 514.5 nm line is only 36% efficient with respect to the maximum of rose bengal absorption, this laser is much more powerful (by at least a factor of 1000) and versatile than the He-Ne laser. The argon ion laser has been found to be useful in occluding arteries of all diameters.

The argon-pumped dye laser is a very efficient source of excitation for rose bengal. The argon laser beam is focused on a jet stream of an organic dye; the argon laser light is absorbed and another laser beam is produced which has the property of wavelength tunability. This property enables the dye laser to be set at the optimal wavelength for the excitation of rose bengal. Thus, laser light at 562 nm is easily obtained, and rose bengal is thereby excited at the peak of its absorption spectrum in tissue.

Using the argon-pumped dye laser, a gain in efficiency of endothelial photosensitization of at least a factor of 3 is realized over the 514.5 nm argon laser line. In practice, the overall improvement in photothrombotic efficiency may be much greater than 3, owing to the nonlinear nature of the platelet chain-reaction response. Using the 514.5 nm argon laser line, an initial concentration of rose bengal in the blood of, for example, about 130 $\mu$M to about 680 $\mu$M can be advantageously used to induce the permanent occlusion of arteries. If an argon-pumped dye laser is tuned to produce a 562 nm laser line, however, at least the same efficiency of photothrombosis is expected for rose bengal in the concentration range of about 45 $\mu$M to about 230 $\mu$M.

In general, the concentration of rose bengal dye in the blood is in an amount sufficient to induce photochemical injury to the vascular endothelium at the point of interaction of the rose bengal with the light beam, which is preferably a laser light beam. Factors affecting the effective concentration range of rose bengal in the blood include laser intensity, the diameter of the artery undergoing occlusion and blood flow rate in the artery. For example, the initial concentration of rose bengal can be adjusted downward when occluding small arteries of about 200 $\mu$m or less, such as those seen in corneal neovasculature, as the process of thrombosis is more efficient in arteries of small diameter. Proper adjustment of the concentration range of rose bengal dye based on the interaction of the above-mentioned factors can be easily determined by .e with ordinary skill in the art.

An initial concentration range of rose bengal dye in the blood of about 340 $\mu$M to about 680 $\mu$M can be advantageously used for occluding 200 $\mu$m diameter arteries when a very low power (1 mW) 543.5 nm He-Ne laser is used to provide the light absorbed by the rose bengal. The initial concentration ranges of rose bengal dye in the blood which can be advantageously used with an argon ion laser and an argon-pumped laser have been noted above. Such concentration will not generally exceed 650 $\mu$M and usually will be significantly lower down to, for example, 45 $\mu$M or even lower, depending on other factors involved, e.g., laser wave length, animal species, and vessel diameter.

During the photothrombotic procedure, irradiation can be initiated simultaneously with or subsequent to rose bengal transfusion. It must be borne in mind, however, that rose bengal is filtered from the blood by the liver. In humans, its disappearance in time from the blood is characterized by three exponentially decaying components. The highest amplitude component is also the fastest decaying component; its half-life (time for the blood concentration to reach one-half the initial value) in humans is eleven minutes (J. Pirotte, *Biomedicine*, 32:17–21, 1980). In rats and rabbits, the half-life is much shorter, being only two minutes and three minutes, respectively (C. D. Klaassen, *Toxicology and Applied Pharmacology*, 38:85-100, 1976). Accordingly, while initial concentration for the rose bengal dye in a range of about 130 $\mu$M to 680 $\mu$M has been demonstrated above for experimental animals, it is contemplated that lower initial concentrations could be effectively employed in humans, particularly in view of the longer half-life of the dye in humans and by appropriate selection of a laser which provides efficient excitation of the rose bengal dye.

Irradiation can be intermittent or continuous. In ophthalmic applications, typical irradiation includes pulses of argon laser light, with the argon laser operated at an effective power level of 300–700 mW and a minimum focused spot diameter of 50 $\mu$m (m=microns). Ophthalmologists very commonly irradiate in the pulsed mode, by pressing a foot switch. In this mode, the location of each pulse may be adjusted in order to realign the targeted tissue, and thereby compensate for the effect of eye movements. Continuous irradiation might damage adjacent structures, and it is impossible to track a small vessel and irradiate it accurately over several seconds. That corneal new vessels can be occluded using the photothrombotic technique with laser parameters familiar to ophthalmologists (especially the pulsed mode) is a tremendous advantage. It could not have been predicted prior to the invention that the concentration of proaggregant secretions from platelets adhering to the photodamaged endothelium would exist at the irradiated site long enough, between laser pulses, to facilitate deposition of more platelets.

During operation of the laser light beam, no special precautions need to be taken. There are no penetrating effects similar to those of ionizing radiation. The chief agent of damage under usual conditions is a thermal burn, on the tissue surface, of limited depth. In ophthalmic applications, shielding of adjacent tissue by means of a template is unnecessary. In neurosurgery, however, a device which can receive the scattered portion of the irradiating beam may be necessary, in order to protect adjacent nervous tissue from the high intensity beams likely to be employed in the occlusion of arteries which are considerably larger than those in the eye.

Following photothrombotic treatment, it is contemplated that the patient can be released within a couple of hours and can travel normally outdoors without fear of becoming systemically photosensitized. The dye disappears through the feces in 3 days. This is not the case with the popularly used dihematoporphyrin ether derivative dye used for phototoxic tumor therapy; the half life of this dye is so long that it is necessary for one undergoing phototoxic tumor therapy using this dye to remain indoors and out of the sun for a month.

The occlusion of an artery by a platelet (white) thrombus is signaled by the development of a colorless segment that will be seen at the site of the thrombus. Downstream, the artery will often blanch (especially in the case of corneal new vessels up to 80 $\mu$m in diameter), indicating drainage of that blood which got past the forming thrombus before occlusion took place. For arteries of the order of 200 $\mu$m in diameter, such as the rat middle cerebral artery, the downstream blood remains in place owing to resistance from the rest of the vascular network and/or the activation of collateral channels (new routes for blood entry into the area formerly supplied by the artery).

In another embodiment of the invention, it has been found that erythrosin B can be used in the same fashion as rose bengal as a photosensitizer in the photochemical occlusion of arteries. Generally, the concentration of erythrosin B dye in the blood is in an amount sufficient to induce photochemical injury to the vascular endothelium at the point of interaction of the erythrosin B with the light beam, which is preferably a laser light beam. As in the case of rose bengal dye, the interaction of factors such as laser intensity, the diameter of the artery undergoing occlusion and blood flow rate affect the effective concentration range of erythrosin B in the blood.

In experiments performed by the inventor using an argon ion laser, erythrosin B, administered intravenously at a blood concentration of 680 $\mu$M, was used to photothrombotically occlude the rat middle cerebral artery in the same fashion as rose bengal.

The absorption maximum of erythrosin B in endothelial tissue is at 536 nm, which is closer than that of rose bengal to the standard 514.5 nm wavelength of the argon ion laser. Thus, although its quantum efficiency for singlet oxygen production is slightly less, erythrosin B can operate with comparable photothrombotic efficiency in vivo when the 514.5 nm argon line, for example, is used to excite it.

To enhance the efficiency of erythrosin B as a photosensitizing agent, another argon laser transition at 528.7 nm (which is closer to the erythrosin B maximal absorption wavelength) has been used to photoexcite erythrosin B. In an ordinary 4 watt argon ion laser, powers of up to 400 milliwatts can be obtained from the 528.7 nm transition. With an argon-pumped dye laser, the laser light can be set at 536 nm, thereby exciting the erythrosin B at the peak of its absorption spectrum in tissue.

The present invention will be illustrated in detail in the following examples. These examples are included for illustrative purposes and should not be considered to limit the present invention.

EXAMPLE 1

The common carotid, femoral and middle cerebral arteries in the rat were occluded thrombotically by means of a rose bengal dye-sensitized photochemical reaction initiated in vascular endothelium by the beam of an argon laser focused for maximum excitation efficiency of the photosensitizer according to a derived criterion.

1. Methods and Materials

Male Wistar rats, each weighing 280 to 330 gm, were anesthetized with 1.5% halothane and maintained on a 70:30 mixture of nitrous oxide and oxygen delivered by a closely fitting Mylar face mask (Watson et al., *J. Neurosurg.*, 66:748-754, 1987, the disclosure of which is hereby incorporated by reference and relied upon). After separation of the temporal musculature, the middle cerebral artery was exposed via a small subtemporal craniectomy produced by a high-speed drill under an operating microscope; the dura was left intact. The common carotid arteries were exposed bilaterally by a midline incision extending from the mental process to the sternal notch; the sternocleidomastoid muscle was then retracted laterally to expose the underlying artery. Bleeding from the operative site was controlled with pressure and Gelfoam. The animal was then prepared for irradiation by filling the surgical cavity with saline, just submerging the exposed blood vessel. The saline solution was kept clear by frequent suction and irrigation. The femoral arteries were exposed by bilateral inguinal incisions and were prepared for irradiation in a fashion similar to that described above.

A tunable argon ion laser (a Lexel Model 95 argon ion laser, manufactured by Cooper LaserSonics, Santa Clara, Calif.), operated at 514.5 nm, was used for the irradiation. The argon ion laser was focused according to a derived criterion (described below) to facilitate maximally efficient intraluminal growth of the occlusive thrombus. The middle cerebral artery was irradiated with 7.5 mW delivered either continuously or via a beam-chopper operated at 200 Hz (with 75 mW peak power, 10% duty cycle). The carotid and femoral arteries were each irradiated with a chopped beam at 1 W average power (2 W peak power chopped at 200 Hz and 50% duty cycle). The laser light beam was focused onto the artery according to the optimization criterion derived analytically as shown below, and the irradiated segment was observed at $\times 32$ magnification through an operating microscope fitted with a 514-nm rejection interference filter. The middle cerebral artery (diameter approximately 200 $\mu$m) was irradiated through a spherical lens of 39-cm focal length at a distance of 40 cm from the artery; with correction for optical reflection losses, the incident intensity was 16 W/sq cm. The femoral artery (diameter 670 $\mu$m) and common carotid artery (diameter 800 $\mu$m) were irradiated through a spherical lens of 61-cm focal length at distances of 42 and 26 cm from the artery, respectively. In each case, the average incident intensity, with correction for irradiation geometry, was approximately 160 W/sq cm.

A stock solution of rose bengal dye, 30 mg/ml in 0.9% saline, was made up for intravenous injection (via the tail vein) at a dose of 40 mg/kg. Before dye injection, the contralateral (control) arteries were irradiated for 15 minutes at the stated intensities. Following this, simultaneous intravenous infusion of the rose bengal solution (at 20 mg/kg/min over 2 minutes) and irradiation of the ipsilateral artery was begun. Five rats were used for common carotid artery irradiation and four for femoral artery irradiation. In the latter case, two rats received only 20 mg/kg. Middle cerebral artery irradiation was performed in a large series of approximately 70 animals.

Thrombus development and subsequent occlusion of the middle cerebral artery were easily observed during irradiation owing to wall transparency. The irradiated segment emitted a bright orange fluorescence (as viewed through an interference filter which rejected the 514.5 nm argon line); this was attributed to rose bengal uptake by red blood cell membranes and binding to plasma proteins such as albumin. As the irradiation proceeded, the fluorescence became yellowish and less intense owing to the accumulation of platelets and exclusion of red blood cells from the developing thrombus. Complete occlusion was signaled by exclusion of red blood cells from the arterial segments both distal and proximal to the irradiated portion, leaving a single colorless segment 7 to 10 arterial diameters in length. Five minutes after completion of irradiation, during which the thrombus was allowed to stabilize, the integrity of the thrombus was tested by injection of a 200 μm bolus of saline solution into a retrograde external carotid artery catheter; no recanalization was observed.

As assessed by observation of rose bengal fluorescence, thrombus development in the common carotid or femoral arteries followed a course similar to that observed in the middle cerebral artery, except that the thrombus appeared as a reddish-brown plug as viewed through the blood vessel wall. Intense scattering of the incident laser light was also noted at about the time that arterial pulsations at the level of irradiation ceased. The conjunction of these events was found to signify the end point for complete occlusion, as verified by a pulse injection of saline via the subclavian artery.

Ultrastructural studies were carried out at either 30 minutes or 7 days following irradiation. Animals were perfused transcardially with 0.9% sodium chloride solution followed by 2% paraformaldehyde and 2.5% glutaraldehyde in a 0.1 M sodium phosphate buffer. Perfusion pressure was monitored throughout the procedure and was maintained at 100 mm Hg. After perfusion fixation, the femoral and common carotid arteries were isolated and placed in fixative for an additional 2 hours. To isolate the middle cerebral artery, the brain was first removed from the cranial vault and placed in fixative for a 2-hour period. Next, the whole brain was placed in phosphate-buffered 1% osmium tetroxide for 2 minutes. This step resulted in the staining of the wall of the middle cerebral artery and aided in blood vessel identification and isolation (Dietrich et al., *Am. J. Physiol.*, 238: H172–H175, 1980). Specimens were next returned to chilled 0.1 M sodium phosphate buffer (4° C.) for 2 hours.

The blood vessels were then postfixed in Millonig's phosphate-buffered 1% osmium tetroxide for 1 hour. Specimens chosen for transmission electron microscopy were dehydrated in ethanol and propylene oxide and embedded in Poly-Bed 812 as previously described (Dietrich et al., *J Neuropathol. Exp. Neurol.*, 43:72–83, 1984). Sections 1 μm thick were cut with glass knives on a Sorvall ultra-microtome and stained with toluidine blue. To characterize the occlusive material more completely, ultra-thin sections stained with uranyl acetate and lead citrate were examined with a Zeiss EM-10C electron microscope. The blood vessels chosen for scanning electron microscopy analysis were examined under a dissecting microscope and cut longitudinally with a scalpel blade to expose the luminal surface. The blood vessels were then dehydrated in graded ethanols and placed in Freon. The tissue was critical-point dried, coated with gold, and examined and photographed with a JEOL JSM-35C scanning electron microscope.

2. Deduction of Optimum Focus

In order to effect complete blood vessel occlusion initiated by an intra-endothelial photochemical reaction, it was assumed that the endothelial-bound photosensitizing dye must absorb the incident laser light beam with maximum efficiency. How this should be done was not obvious because the laser beam impinged with a cross-sectionally non-uniform intensity onto the cylindrical blood vessel surface. With the laser operating in the fundamental (gaussian) mode (Kogelnik et al., *Appl. Optics*, 5:1550–1567, 1966), the most effective focusing condition was deduced (from Equation 6 below) in terms of a focusing criterion. For the purposes of illustration, the focusing criterion is expressed here in only one dimension, designated by x. The direction of incidence (y-direction) of the laser beam onto the blood vessel was perpendicular both to the blood vessel axis (z-direction) and to the x-direction, collinear with the vessel diameter. The normalized intensity distribution $G(x)$ of the laser beam, viewed transversely to the direction of incidence was $$G(x) = Kw^{-1}e^{-2x^2/w^2} \qquad (1)$$

where $K = (2/\pi)^{\frac{1}{2}}$ and w defines the distance at which the intensity falls to $e^{-2}$ of its maximum.

The light-absorbing dye was distributed in the endothelium, around the circumference of the blood vessel of radius R. The linear density $L_0$ of dye molecules was thus expressed as $$L_0 = N/(\pi R) \qquad (2)$$

where N is the total number of molecules. As viewed along the direction of incidence, however, the distribution of absorbing molecules could be expressed in terms of the transverse x direction as a function, $L(x)$:

$$L(x) = RL_0/(R^2 - x^2)^{\frac{1}{2}} \qquad (3)$$

The interaction of the incident laser beam with the dye population, summed over the half-circumference of the subject blood vessel, was given by $$F(R,w) = C \int_{-R}^{R} G(x)L(x)dx \qquad (4)$$

where $F(R,w)$ is the function describing the absorbance of the incident laser beam by the endothelial-bound dye molecules, and C is a constant that includes the incident laser beam intensity and the molar absorption coefficient. Substitution of $x = R\cos\theta$ and integration over angle coordinates yielded $$F(q) = KCqe^{-q^2}I_0(q^2) \qquad (5)$$

in which, for simplicity, R/w was designated by q and $I_0(q^2)$ is the zero-order modified Bessel function of the first kind (Olver, *Handbook of Mathematical Functions with Formulas, Graphs and Mathematical Tables*, Washington D.C.: U.S. Government Printing Office, 1964, pp. 355–454).

For maximally efficient excitation of the rose bengal dye by optimum focusing (optimum ratio of R/w) the function F(R/w), equivalent to F(q), had to be maximized. This was done by differentiating F(q) and setting the result to zero:

$$I_1(q^2)/I_0(q^2) = 1 - (2q)^{-1} \qquad (6)$$

where $I_1(q^2)$ is the first-order modified Bessel function of the first kind (Olver, *Handbook of Mathematical Functions with Formulas, Graphs and Mathematical Tables,* Washington D.C.: U.S. Government Printing Office, 1964, pp. 355–454). This equation was solved graphically with the aid of Bessel function tables (Olver, *Handbook of Mathematical Functions with Formulas, Graphs and Mathematical Tables,* Washington D.C.: U.S. Government Printing Office, 1964, pp. 355–454) to yield $q_{max} = (R/w)_{max} = 0.89$ (that is, $w = 1.12R$).

For optimum focusing, the laser beam diameter (2w) had to overlap the subject blood vessel by 6% on each side. To determine the percentage of incident light intercepted by the blood vessel, Equation 1 (with $w = 1.12R$) was integrated between $\pm R$; this result was divided by the integral of Equation 1 between $\pm \infty$; the ratio was 92.5%. The percentage that was lost past the edges of the blood vessel was therefore only 7.5%. The calculation suggested that the photochemical contribution of dye molecules located toward the edges of the blood vessel was significant, and implied that focusing the beam within the arterial diameter, away from the edges, was photochemically inefficient.

3. Results

Photochemically induced thrombotic occlusion was always observed in irradiated arteries of rats injected with rose bengal solution. In both the common carotid artery and the femoral artery, vasoconstriction was present and the lumen of the artery was entirely filled by a thrombus of mixed character. Islands of aggregated platelets were seen interspersed among clumps of red blood cells and an amorphous material (coagulum). A mixture of red blood cells and coagulum extended distally for at least 10 arterial diameters. The recorded average temperature of 84° C. ±4° C. (± standard deviation) in the cores of the completed common carotid artery occlusions was sufficient to induce the secretion of coagulum. Generally, complete occlusion of each artery occurred within 3 minutes of irradiation; the femoral arteries of the two rats injected with one-half the standard dose were occluded within 4 minutes. The total energy deposited at occlusion was 140 to 180 joules (J), while the corresponding energy fluence (total energy deposited per unit area; Boulnois, *Lasers Med. Sci.,* 1:47–66, 1986) was about 35 kJ/sq cm.

A white thrombus resulting from the photochemically induced occlusion of the middle cerebral artery, was shown by ultrastructural analysis to be composed primarily of aggregated platelets. Longitudinal corrugations in the artery wall resulted from vasoconstriction. The platelet mass appeared to be uniform in density, but overt fibrin strands were not associated with it. The irradiation time to effect complete occlusion at the very low incident intensity used was again 3 minutes or less. The total energy deposited and energy fluence in this case were approximately 1 J and 3.5 kJ/sq cm, respectively.

The results indicate that small arteries, such as the small penetrating arteries that feed an arteriovenous malformation (AVM), should be amenable to occlusion using the photothrombotic method. The results also demonstrate that the occlusion of larger arteries is entirely achievable within the output capacity of a commonly available argon ion laser when used in conjunction with systemically jected rose bengal dye. No damage of any kind, including wall damage due to possible heat absorption, was observed during or following irradiation of the small arteries (200 μm or less in diameter), or in larger arteries (over 600 μm in diameter) provided the larger arteries were irradiated under water (saline solution), as described above.

EXAMPLE 2

In order to test the role of systemically injected rose bengal dye in inducing photochemical injury to vascular endothelium, the general procedure described above in Example 1 was repeated, with the exception that rose bengal dye was not injected into the bloodstream.

In the absence of rose bengal dye, irradiation at equivalent beam intensities of the common carotid, femoral and middle cerebral arteries in the rat was completely ineffective in inducing structural or functional damage of the arteries. Accordingly, occlusion of these arteries did not take place.

These results clearly show that rose bengal dye must be present in the vasculature in order to achieve the photothrombotic effect.

EXAMPLE 3

The photothrombotic method of Example 1 was modified in order to occlude small arteries at normal blood pressure.

1. Method and Materials

In order to conduct irradiation of the rat middle cerebral artery at normal blood pressure, oral intubation was performed and mechanical ventilation was initiated after paralysis with pancuronium bromide. The rat was then placed on a tiltable stereotaxic frame, and the middle cerebral artery was exposed through a subtemporal approach. The right temporalis musculature was reflected anteriorly, and a 2×2 mm subtemporal craniotomy was carried out with the aid of a high-speed drill under a dissecting microscope, leaving the middle cerebral artery exposed and the dura intact at the level of the olfactory tract. Rose bengal dye (2 mg in 0.133 ml saline per 100 g animal weight) was administered intravenously, resulting in a blood concentration of 340 μM.

The right middle cerebral artery, at a point just distal to the olfactory branches, was irradiated with the beam of a tunable argon ion laser (Lexel Model 95, Cooper LaserSonics, Santa Clara, CA), operated at 514.5 nm in the continuous mode at a power level of 50 mW. The beam was focused longitudinally onto the middle cerebral artery with two cylindrical lenses, both of 30 cm focal length. This ensured a beam configuration which spanned the entire middle cerebral artery diameter and extended approximately 0.5 mm along its length; the incident intensity was thus about 50 watts/cm². During irradiation, the irradiated segment appeared orange, owing to rose bengal fluorescence in the flowing blood stream. Irradiation time was of the order of 5 minutes, with the operative criterion being continuous formation of a white thrombus without interruption by spontaneous recanalization.

2. Results

The occluded middle cerebral artery segment, approximately 1 mm in length, was readily visible through the dissecting microscope as a bloodless, nearly colorless segment. The wounds were then closed in layers and the animal extubated, and upon recovery, allowed access to food and water ad libitum.

The results of the procedure show that the method of anesthesia employed in the photothrombotic procedure can affect its outcome. Because systemic anesthesia causes blood pressure to fall, photothrombosis occurs more readily due to the decreased dilution of the platelet secretions.

EXAMPLE 4

The efficacy and safety of the photochemical reaction of the present invention in facilitating permanent occlusion of corneal neovasculature was evaluated as described below.

1. Methods and Materials

Induction of Corneal Neovascularization:

The corneal and limbal epithelia, along with the conjunctival epithelium 2-3 mm beyond the limbus, were removed from New Zealand albino rabbits by a combination of surgical scraping and n-heptanol debridement. The denuded corneal surfaces were then healed by the remaining conjunctival epithelium, of which 65% contained extensive neovascularization. From this group, 16 corneas with neovascularization persistent for about 20 months were subjected to photothrombotic treatment.

Induction of Photothrombosis with Rose Bengal Solution:

Various concentrations of rose bengal (M.W. 1018, certified grade, Aldrich Chemical Co., Milwaukee, Wis.) were dissolved in normal saline and filter-sterilized for intravenous use. The highest concentration which could be achieved practically was 100 mg/ml. The pH of an isotonic saline solution of rose bengal at a concentration of 15 mg/ml was 6.80. Isotonic saline solution was used as a control solution.

After anesthesia with intramuscular injection of xylazine (10 mg/kg bw) and ketamine (10 mg/kg bw), the rabbits were injected intravenously with either 2.5 ml of isotonic saline solution or rose bengal saline solution at a dosage of 40 mg/kg bw. Irradiation of corneal vessels was carried out with an argon ion laser (Model 95, Cooper LaserSonics, Fremont, Calif.) operated at 514.5 nm, as described by Mendelsohn et al. (*Arch. Opthalmol.*, 105:983-988, 1987). The beam focusing apparatus was mounted in an X-Y positioning device attached to a rotary turntable, both with micrometer precision (Daedal, Inc., Harrison City, Pa.). With this apparatus, beam positioning stability and reproducibility of incident intensity were improved because irradiations were administered during the open cycle of the mechanical shutter. The incident power level was set at 200 mW; allowing for reflection losses in the fiber optic focusing system, the incident power was reduced to 130 mW. At the focal point, the laser beam was 63 μm in diameter. Each irradiation was 0.2 second in pulse duration. During the entire procedure, the corneas were continuously rinsed with a balanced salt solution delivered through a peristatic pump and the temperature of the solution was maintained at 37° C. with a water bath. After laser irradiation, topical antibiotics and steroids were applied for two days.

External Photography and Corneal Fluorescein Angiography:

Routine external photography and corneal fluorescein angiography were performed to document occlusion of the corneal blood vessels and the duration of their occlusion. Angiograms were taken with a ceiling-mounted Zeiss surgical photoscope after injection of 1 ml of 10 mg/ml fluorescein solution. Baseline angiography was performed two or three days before laser irradiation to avoid possible photosensitizing effects from the fluorescein dye used for angiography. After photothrombotic treatment, angiograms were taken on scheduled dates in order to monitor the duration of the occlusive effect. Late phase (5 minutes after injection) fluorescein angiograms were used for comparison.

Immunofluorescence Study of Thrombus Composition:

The composition of photochemically induced thrombi was compared to that of natural clots by means of indirect immunofluorescence studies with antibodies to human fibrinogen and Factor VIII. Frozen sections of rat blood clotted in air, or of a photochemically induced middle cerebral artery thrombus in the rat (Watson et al., *Ann. Neurol.*, 17:497-504, 1985; Watson et al., *J. Neurosurg.*, 66:748-754, 1987; Watson et al., *Cerebrovascular Diseases—Fifteenth Princeton Conference*, Eds. M. E. Raichle and W. J. Powers, New York, Raven Press, pp. 317-330, 1987; were incubated with 1% bovine serum albumin (BSA) in PBS for 30 minutes in order to inhibit non-specific binding. Affinity-purified rabbit antiserum to human fibrinogen (Behring Diagnostics, La Jolla, Calif.) and mouse monoclonal antibody to human Factor VIII (Hybridtech, Inc., San Diego, Calif.) were used as specific primary antibodies. Following incubation with primary antibody for one hour, FITC-conjugated goat anti-mouse IgG and goat anti-mouse IgG antibodies (Sigma Chemical Co., St. Louis, Mo.) were used as secondary antibodies for anti-fibrinogen and anti-Factor VIII, respectively. The sections were observed by epi-illumination with a Nikon Microphot-FX microscope.

Toxicity Study of Intravenous Rose Bengal:

In order to investigate possible systemic side effects of rose bengal, the blood chemistry profiles of healthy rabbits before and after intravenous injection of rose bengal were studied. Four practical dosages, i.e., 40, 16, 8 and 4 mg/kg bw, were administered. Five rabbits were used for each dosage except for the dosage of 40 mg/kg bw, in which case ten rabbits were used. Three blood samples (3 ml each) were collected from each rabbit before injection with rose bengal, and one and five days following injection. External examination on day one after injection revealed a slightly pinkish discoloration of the mucosal surfaces including the nictitating membrane, conjunctiva and nostril, but these effects were not apparent after day two. Neither lethargy nor change of appetite was noted throughout one week of follow-up after injection.

The results of the blood chemistry analyses are summarized in Table 1.

TABLE 1

Effects of Intravenous Rose Bengal on Blood Chemistry

|  | Normal (n = 25) Day 1 | 40 mg/kg BW (n = 10) Day 5 | 16 mg/kg BW (n = 5) Day 1 | |
| --- | --- | --- | --- | --- |
| Glucose (mg/dL) | 114.1 ± 16.6 | 109.4 ± 20.3 | 134.2 ± 28.9 | 125.6 ± 10.7 |
| Sodium (mM) | 143.6 ± 3.7 | 143.2 ± 3.0 | 141.2 ± 1.8 | 144.4 ± 1.5 |
| Potassium (mM) | 4.6 ± 0.6 | 4.3 ± 1.5 | 4.7 ± 0.5 | 4.3 ± 0.3 |
| Chloride (mM) | 104.0 ± 4.6 | 106.0 ± 13.6 | 100.0 ± 4.4 | 101.8 ± 2.8 |
| Carbon Dioxide (mM) | 20.9 ± 3.9 | 20.2 ± 6.5 | 24.5 ± 2.3 | 24.5 ± 3.5 |
| Urea Nitrogen (mg/dL) | 17.0 ± 3.7 | 22.5 ± 4.6[a] | 15.0 ± 3.4 | 15.0 ± 2.6 |
| Creatinine (mg/dL) | 1.4 ± 0.2 | 1.4 ± 0.3 | 1.2 ± 0.2 | 1.4 ± 0.2 |
| Total Protein (g/dL) | 5.1 ± 0.4 | 4.9 ± 0.4 | 5.0 ± 0.3 | 4.8 ± 0.1 |
| Albumin (g/dL) | 4.1 ± 0.4 | 3.9 ± 0.3 | 3.7 ± 0.3 | 3.7 ± 0.1 |
| Total Bilirubin (mg/dL) | 0.7 ± 0.1 | 1.3 ± 0.8[b] | 0.7 ± 0.1 | 0.8 ± 0.1 |
| Calcium (mg/dL) | 13.6 ± 0.9 | 13.7 ± 0.9 | 13.6 ± 0.7 | 13.9 ± 0.2 |
| Phosphorous (mg/dL) | 6.4 ± 0.7 | 5.2 ± 1.3[c] | 6.1 ± 0.5 | 6.1 ± 0.2 |
| Alk. Phosphatase (IU/L) | 121.4 ± 42.4 | 403.6 ± 306.0[d] | 121.0 ± 41.2 | 105.2 ± 26.3 |
| SGPT (IU/L) | 61.4 ± 14.9 | 434.5 ± 328.5[e] | 89.4 ± 22.0 | 75.2 ± 18.6 |
| SGOT (IU/L) | 40.6 ± 10.7 | 154.6 ± 112.0[f] | 36.6 ± 5.6 | 32.4 ± 9.0 |
| Amylase (U/L) | 233.7 ± 37.7 | 365.6 ± 338.0 | 216.0 ± 44.6 | 237.0 ± 28.1 |
| Cholesterol (mg/dL) | 81.8 ± 24.9 | 106.0 ± 44.5 | 128.8 ± 39.1 | 98.2 ± 10.4 |

[note]:
[a] $p < 0.005$;
[b] $p < 0.05$;
[c] $p < 0.02$;
[d] $p < 0.02$;
[e] $p < 0.01$;
[f] $p < 0.02$ A review of Table 1 shows that compared with the normal control pooled data from 25 healthy rabbits without injection, all analyses were within the normal range except for a small number in the group that received the highest dosage of 40 mg/kg bw.

Efficacy of Photothrombosis with Different Concentrations of Rose Bengal;

Various dosages of rose bengal solution were used to investigate the efficacy of photothrombosis. The results are summarized in Table 2.

TABLE 2

Total Laser Shots to Occlude each Vessel

| Duration (min) | Dosage of I.V. Rose Bengal (mg/kg BW) | | | |
| --- | --- | --- | --- | --- |
|  | 40 | 16 | 8 | 4 |
| 0–10 | 5 ± 1 | 8 ± 3 | 13 ± 4 | 33 ± 8 |
| 10–20 | 5 ± 1 | 9 ± 2 | 19 ± 1 | 53 ± 8 |
| 20–30 | 6 ± 1 | 10 ± 2 | 30 ± 4 | 81 ± 11 |
| 30–40 | 8 ± 2 | 13 ± 3 | 51 ± 7 | >100 |
| 40–50 | 10 ± 3 | 20 ± 4 | 65 ± 6 | N.O. |
| 50–60 | 15 ± 4 | 32 ± 5 | 85 ± 10 | N.O. |

[note]:
1. N.O.: not occluded
2. Laser setting: 514.5 nm; 200 mW; 63 μm; 0.2 sec.
3. Data are expressed as means ± s.d. from three different blood vessels of the same cornea At the same laser irradiation settings used in this study, the vessels could be occluded effectively with a dosage as low as 8 mg/kg bw given in one bolus. The irradiation period could be extended to at least one hour after the injection, although with decreased occlusive efficacy. At the dosage of 4 mg/kg bw, the vessels could still be occluded within 30 minutes, provided that sufficient shots were applied. In view of practical clinical circumstances, application of more than 30 shots to achieve occlusion of a single vessel was considered to exceed the limit of effectiveness in this study.

Because fewer than 20 shots per target vessel at 8 mg/kg bw or higher dose of rose bengal were required to achieve photothrombotic occlusion, an experimentation time of one hour was sufficient for treatment of extensively vascularized corneas. Consequently, it was not necessary to administer a booster injection of rose bengal solution in order to maintain a blood level sufficient to mediate the photothrombotic effect. The fact that more than 100 shots were required to occlude blood vessels at the dosage of 4 mg/kg bw further supports the notion that photocoagulation, i.e., irradiation (without rose bengal) at the present settings could not achieve effective occlusion.

3. Results

Clinical Observations During Photothrombosis:

Immediately after the completion of photothrombosis, the treated upper cornea remained relatively clear of rose bengal but the untreated lower cornea was infiltrated subsequently with extravasated dye. One day after treatment with photothrombosis, the rabbit conjunctiva became edematous and slightly pinkish in color, presumably due to the retention of extravasated rose bengal. The condition was effectively managed by topical steroids and antibiotics; the corneas returned to a normal appearance within two or three days. This side effect was noted only in rabbits injected with 40 mg/kg bw rose bengal, but not in those with lower dosages, indicating that this side effect is a dose-dependent phenomenon.

One week after irradiation, the occluded corneal vessels gradually involuted and the corneal surface of the treated area became smoother, with improved corneal clarity. The visibility of iris details was notably enhanced after treatment.

Occlusion of corneal vessels was also confirmed by corneal fluorescein angiography. Abundant corneal vessels with diffuse extravasation of fluorescein dye were invariably observed on the vascularized corneas prior to treatment. After photothrombosis, the treated vessels were completely occluded without any dye leakage. The vessels remained occluded, as demonstrated in the follow-up angiograms, and gradually involuted without recanalization or stimulation of new vessel formation elsewhere during the four-month study period.

Immunofluorescence studies of naturally coagulated rat blood demonstrated only faint background staining for fibrinogen and Factor VIII, indicating that only trace amounts of these consumable, essential clotting factors appear in the natural clot. In contrast, rose bengal-photoinduced middle cerebral artery thrombi displayed an abundance of fibrinogen and Factor VIII indicating that neither the extrinsic nor intrinsic clotting systems were activated, thus verifying the absence of fibrin.

The results of this experiment demonstrate that corneal neovascularization induced by ocular surface injury can be effectively occluded using the photothrombotic method of the present invention. Provided the initial rose bengal concentration is in the range of 8 mg/kg bw or higher, the photothrombotic effect is readily achieved in corneal new vessels with incident argon laser settings much lower than those of conventional photocoagulation. In addition, as shown by Table 1, intravenous administration of rose bengal does not result in long-term systemic toxicity.

EXAMPLE 5

Previous studies have established that conjunctival transdifferentiation is inhibited by corneal vascularization. Conversely, occlusion of corneal blood vessels can induce conjunctival transdifferentiation on vascularized corneas, as evidenced by a total loss of goblet cells on the corneal surface. To test this hypothesis, the following experiment was performed.

1. Methods and Materials

Experimental Model of Vascularized Corneas with Conjunctival Transdifferentiation Defect:

Both corneal and limbal epithelia, along with the conjunctival epithelium 2-3 mm beyond the limbus, were removed from New Zealand albino rabbit eyes by n-heptanol debridement and surgical scraping (Huang et al., *Ophthalmology*, 95:228-235, 1988, the disclosure of which is hereby incorporated by reference and relied upon). The denuded corneas were healed by the remaining conjunctival epithelium within 9 to 12 days, of which 65% became extensively vascularized two to three weeks after healing. Sixteen corneas with persistent neovascularization of 20 months duration were subjected to photothrombotic treatment.

Occlusion of Corneal Vessels by Photothrombosis:

Rose bengal solution at a concentration of 30 mg/ml was prepared by dissolving the rose bengal (M.W. 1018, certified grade, Aldrich Chemical Co., Milwaukee, Wis.) in normal saline solution, and filtering via a 0.45 μm sterile Millipore ® filter (Medford, Mass.). Occlusion of corneal blood vessels was achieved by intravenous injection of the rose bengal solution at a dosage of 40 mg/kg body weight followed by irradiation of the blood vessels with an argon green laser beam (514.5 nm in wavelength) set at a power of 130 mW, beam spot size of 63 μm in diameter, and duration of 0.2 second. During the irradiation, the corneal surface was rinsed with a balanced salt solution maintained at 37° C. to ensure the efficacy of photothrombosis. The laser beam was applied to the limbus at the arborization point of each feeder vessel. In 12 corneas, the blood vessels on the upper half of the cornea were photothrombosed and those on the lower half were left untreated and used as an internal control. In the remaining four corneas, the blood vessels on the entire cornea were treated. Each blood vessel was occluded within 10 consecutive shots of irradiation. For all corneas, the treatment was completed within 30 minutes after initial injection of rose bengal solution. After laser irradiation, topical antibiotics and steroids were applied for two days. This treatment was similar to that described in Watson et al., *Lasers Surg. Med.*, 7:127, 1987.

Clinical Observations and Corneal Fluorescein Angiography:

External ocular examinations were performed to identify changes on the ocular surface before and after photothrombosis. Surface smoothness was examined by routine slitlamp biomicroscopy. External photographs were taken to document corneal clarity and regression of the vessels.

Occlusion of the corneal blood vessels and the duration of occlusion were further studied by routine corneal fluorescein angiography using an intravenous injection of 1 ml of 10 mg/ml of sodium fluorescein. Photographs and angiograms were taken with a Zeiss surgical microscope. Baseline angiography was performed two to three days before photothrombosis to avoid possible photosensitizing effects from the fluorescein used for angiography. Follow-up angiograms were taken on the scheduled dates to document the occlusive effect and its duration. Late phase fluorescein angiograms (5 minutes after injection) were chosen for comparisons. After occlusion was confirmed by angiography, the rabbits were sacrificed on the prescheduled date and corneal buttons were obtained and subjected to epithelial differentiation studies. The total follow-up duration was 18 weeks.

Studies of Epithelial Differentiation on Photothrombosed Corneas:

In order to study the goblet cell density on the vascularized corneas before and after photothrombosis, corneal flat-mounts were prepared and stained according to usual methods (Tseng et al., *Invest. Opthalmol. Vis. Sci.*, 25:1168-76, 1984). The pattern of goblet cell disappearance was then analyzed and specifically correlated with the treated area.

The epithelial phenotype of the control and treated corneas was then studied by impression cytology (Tseng, *Ophthalmology*, 92:728-33, 1985) and routine histology using hematoxylin and PAS. In addition, immunofluorescent stainings of the frozen sections using a previously developed anti-rabbit ocular mucin monoclonal antibody [anti-ROM] was performed to study mucin expression.

2. Results

Clinical Observations After Photothrombosis:

As noted above, sixteen corneas with extensive neovascularization persistent for 20 months were subjected to photothrombosis. In 12 corneas, blood vessels on the upper half of the cornea were photothrombosed. Immediately after treatment, the treated areas cleared of rose bengal in all 12 corneas, whereas the untreated areas were infiltrated with the pinkish color of extravasated rose bengal. In the remaining four corneas, the blood vessels on the entire cornea were treated. The central cornea was free of rose bengal infiltration; the pinkish discoloration was noted only around the limbus. One day after photothrombosis, all 16 corneas were clear of retained rose bengal. Hemorrhagic spots were noted on some corneas, presumably due to venous congestion; these spots usually persisted for only two to three days after treatment. Four days after treatment, the occluded corneal blood vessels gradually regressed and the corneal surface of the treated area became relatively smooth and lustrous.

The corneal integrity further improved with time. Following treatment, the blood vessels were involuted from the central corneas, and visibility of iris details was improved. No epithelial breakdown was observed during the entire study period.

To further confirm the effect and duration of blood vessel occlusion by photothrombosis, corneal fluorescein angiography was performed before and after treatment. Late phase corneal angiograms were used for comparison. Diffuse extravasation of fluorescein dye from the vascular plexus was invariably observed on the entire cornea prior to treatment. After photothrombosis, the treated areas were free of dye leakage, as demonstrated in follow-up angiograms. In two corneas that were observed for the longest period of 18 weeks, all treated vessels remained occluded without recanalization, and no new vessel growth elsewhere was observed.

Studies on Epithelial Differentiation:

In order to study the impact of blood vessel occlusion on conjunctival epithelial differentiation, corneal flatmounts were prepared to analyze goblet cell density. Before photothrombosis, numerous goblet cells were noted on the entire surface of the vascularized corneas. The goblet cell density was highest in the peripheral cornea, and gradually decreased toward the central cornea. This result was consistent with previously reported findings (Tseng et al., $Invest.$ $Ophthalmol.$ $Vis.$ $Sci.$, 25:1168-76, 1984; Huang et al., $ARVO$ $Abstracts$ $Invest.$ $Ophthalmol.$ $Vis.$ $Sci.$, 27(Suppl.):54, 1986; Tseng et al., $Ophthalmology$, 91:545-52, 1984; Tseng et al., $Invest.$ $Ophthalmol.$ $Vis.$ $Sci.$, 28:538-42, 1987; and M. Farazdaghi et al., $Invest.$ $Ophthalmol.$ $Vis.$ $Sci.$, 25(Suppl.):76, 1984). In contrast, the goblet cell density was remarkably decreased in a centrifugal pattern in the treated areas four days after treatment. The density further decreased with time and no goblet cells were noted on the cornea four weeks after treatment.

To monitor the progression of epithelial transformation, impression cytology (Tseng, $Ophthalmology$, 92:728-33, 1985) and routine histology were employed. Before treatment, impression cytology disclosed numerous goblet cells interspersed among small epithelial cells which had a nuclear:cytoplasm (N/C) ratio of 1:1 on vascularized corneas. Histology showed that the epithelium overlying the vascularized corneal stroma displayed conjunctival characteristics containing goblet cells. One week after treatment, the cytology specimens demonstrated decreased goblet cell density with a slight increase of epithelial N/C ratio. At this time, the histology specimens showed early stratification of epithelial cells with sporadic presence of vacuolated goblet cells. Four weeks after treatment, cytology showed uniformly squamous superficial epithelial cells with a N/C ratio of $\frac{1}{3}$ to $\frac{1}{4}$, without any goblet cells, and histology demonstrated a stratified cornea-like epithelium.

To further confirm the transition of epithelial differentiation, a monoclonal antibody against rabbit ocular mucin [anti-ROM] was used to examine the expression of mucin, the major product of goblet cells. By indirect immunofluorescence studies, expression of mucin antigen was found to diminish gradually with time after vessel occlusion. The complete absence of mucin in the epithelium of the occluded corneas was noted four weeks after treatment.

The results of this experiment demonstrate that photothrombosis can prolong the duration of occlusion of corneal new vessels and induce conjunctival transdifferentiation on vascularized corneas. While attempts to occlude corneal neovascularization by conventional photocoagulation have often elicited concomitant inflammatory reactions and subsequent stimulation of new blood vessel formation (Cherry et al., $Ann.$ $Ophthalmol.$, 5:911-20, 1973; Reed et al., $Arch.$ $Ophthalmol.$, 93:1017-19, 1975; and Mendelsohn et al., $Ophthalmic.$ $Surg.$, 17:502-8, 1986), the photothrombotic technique avoids these potential complications and eliminates the necessity for retreatment. In addition, corneal new vessels are effectively occluded without recanalization or new growth elsewhere.

EXAMPLE 6

The photochemical reaction of the present invention was employed in initiating permanent thrombotic occlusions in the corneal neovasculature of rabbit eyes with experimentally induced lipid keratopathy.

1. Methods and Materials

Nine New Zealand white strain rabbits weighting 1 to 2 kg were rendered hypercholesterolemic by foods that contained high levels of cholesterol, as described in Stock et. al., $Arch.$ $Ophthalmol.$, 103:726-730, 1985; and Mendelsohn et al., $Ophthalmic$ $Surg.$, 17:502-508, 1986. Eight days after commencement of the high-cholesterol diet, corneal sutures were implanted in both eyes according to the surgical procedure described in Mendelsohn et al., $Ophthalmic$ $Surg.$, 17:502-508, 1986.

On day 22, slit-lamp photographs and fluorescein angiograms were obtained of all corneas (Mendelsohn et al., $Arch.$ $Ophthalmol.$, 105:983-988, 1987, the disclosure of which is hereby incorporated by reference and relied upon). On the next day, one eye of each rabbit underwent laser surgery, with the other eye serving as a comparative control. Rose bengal dye was dissolved at a concentration of 30 mg/ml in 0.9% saline solution. For the initial injection, the dye solution was administered at a total body concentration of 45 mg/kg. For the two animals in which the procedure took longer than 25 minutes, a booster injection of 15 mg/kg was administered. Irradiations of corneal vessels were carried out with an argon ion laser (Model 95, Cooper Laser-Sonica, Sunnyvale, Calif.) operated in the TEM$_{00}$ mode at 514.5 nm. The beam was directed toward an aluminized mechanical shutter (AW Vincent Associates, Rochester, NY), which reflected it at a right angle through a 514.5-nm custom interference filter with a transmittance of 92% (Omega Optical, Brattleboro, VT) and then through a fused silica lens with a focal length of 7.5 cm for focusing into a 2.5-m fiberoptic cable 400 $\mu$m in diameter. In the optical fiber, the gaussian input beam profile was converted into an output beam. The output was collimated by a plano convex lens 3.5 cm in focal length and focused with a plano convex lens with a focal length of 1.0 cm. The lenses were mounted in a beam telescope attached to an X-Y positioning device (Daedal Inc., Harrison City, Pa.). The beam diameter was measured with a calibrated reticle in the ocular of a $\times 20$ operating microscope. By observing, through a 514.5-nm rejection filter, the fluorescence of a white card impregnated with rhodamine B, the minimum diameter of the organe fluorescent spot at the focal point was determined to be 63 $\mu$m. Combining the transmission efficiencies of the three uncoated lenses (92% per lens, 76% total transmission) with those of the optical fiber and interference filter yielded a system transmission efficiency of 61.5%. This reduced the incident power level of the laser from 215 mW to an effective power level of 132 mW; this corresponded to an incident intensity at the focal point of 4.23 kW/cm$^2$. During shutter closure, irradiations were carried out in 0.2-s intervals. When the shutter was opened, the low-power beam, which was reflected off an optical flat and through the optical system, was used for aligning the next vessel selected for irradiation.

One eye of each rabbit was subjected to laser applications that were directed toward the vascular branching points of the limbal and corneal feeder vessels adjacent to the sites of lipid deposits. The irradiated blood vessel segment was observed through the ×20 operating microcope fitted with the 514.5-nm rejection band interference filter. Initially, the irradiated segment appeared yellow-orange because the fluorescence of rose bengal had been absorbed into erythrocyte plasma membranes and plasma proteins. As platelets accumulated, the fluorescence became yellowish and less intense. The color gradually disappeared due to the exclusion of red blood cells, indicating occlusion of the vessel. A striking event that preceded the thrombus was intense vasoconstriction at the site of irradiation. Constriction of the vessel could be observed following the initial one to three laser shots in each segment. As laser treatment proceeded, the irradiated segment began to assume a mottled appearance due to the superposition of small reddish aggregates on a generally colorless background. The vessel alternately contracted and, to a lesser extent, expanded. Finally, the irradiated segment became completely colorless as the thrombus evolved within the lumen.

On days 25 and 42, two additional sets of corneal slit-lamp photographs and corneal angiograms were obtained. On day 43, the rabbits were killed. Their corneas were removed and bisected so that each half contained essentially an equal quantity of visible lipid deposition. Biochemical analysis of one of the halves of each cornea was performed to determine the quantity of cholesterol deposits according to the technique described in Stock et al., *Arch. Opthalmol.*, 103:726–730, 1985. The other half was fixed in a solution of 10 mol/L sodium cacodylate, 0.1 mol/L paraffin, and 4 mol/L glutaraldehyde. Cryostat sections were prepared and stained with either oil red 0 or hematoxylin-eosin for histologic analysis.

2. Results

Angiograms were taken 21 days after laser treatments to determine the effect of argon laser-induced photothrombosis in the region of corneal neovascularization. The angiograms depicted a complete lack of perfusion by fluorescein in all nine treated rabbit eyes, with about 95% of the treated corneal vessels occluded. In contrast, the neovasculature in the control eyes remained patent. Examination of corneal sections by light microscopy revealed that the irradiated feeder vessels were patent distal to the photochemically induced occlusions but were devoid of blood because of the absence of recanalization. Both acute and chronic inflammatory cells were observed in mild to moderate numbers in comparable concentrations in both the treated and untreated eyes. No signs of inflammation were observed along the limbal vessels, nor were any new vessels formed in response to the photothrombotic treatment. Both the laser-treated and control corneas showed lipid deposition in the superficial, middle, and deep stroma, as evidenced by positive oil red 0 staining.

The quantity of injected dye, the number of laser shots, and the corneal cholesterol contents (CCC's) for pohothrombotically treated and control (untreated) eyes are shown in Table 3.

TABLE 3

Corneal Cholesterol Concentrations

| | | | Corneal Cholesterol Concentration, g of Cholesterol/ 100 g of Corneal Tissue | | | |
|---|---|---|---|---|---|---|
| Rabbit No. | Rose Bengal Dye Dose, mg/kg | No. of Laser Shots | Untreated Eye | Laser-Treated Eye | Difference Between Treated and Untreated Eyes | Difference Between Treated and Untreated Eyes, % |
| 1 | 45 | 90 | 0.394 | 0.250 | 0.144 | −36.5 |
| 2 | 45 | 58 | 0.284 | 0.277 | 0.007 | −2.5 |
| 3 | 60* | 86 | 0.374 | 0.155 | 0.219 | −58.6 |
| 4 | 45 | 64 | 0.313 | 0.237 | 0.076 | −24.3 |
| 5 | 45 | 90 | 0.357 | 0.208 | 0.149 | −41.7 |
| 6 | 60* | 106 | 0.398 | 0.192 | 0.206 | −51.8 |
| 7 | 45 | 100 | 0.361 | 0.256 | 0.105 | −29.1 |
| 8 | 45 | 96 | 0.307 | 0.178 | 0.129 | −42.0 |
| 9 | 45 | 76 | 0.265 | 0.207 | 0.058 | −21.9 |

*Rabbit received 45 mg/kg and booster shot of 15 mg/kg 25 minutes later.

The laser-treated eyes demonstrated 36% less corneal cholesterol than did the control eyes. The number of laser shots required to occlude the corneal neovasculature varied from 58 to 106 per quadrant, with an average of 85. In general, the number of laser shots required was proportional to the CCC in the untreated eye. Linear regression analysis of the relationship between the required number of laser shots and the CCC of the corresponding untreated eye yielded a correlation coefficient of 0.689 (Mendelsohn et al., *Arch. Ophthalmol.*, 105:983–988, 1987), the disclosure of which is hereby incorporated by reference and relied upon). A plot of the apparent reduction in CCC, defined as the difference in CCC between treated and untreated eyes, against the CCC of the untreated eye revealed a correlation coefficient of 0.819. When the percentage reduction in CCC, calculated as 100 times the differences in CCC between the treated and untreated eyes divided by the CCC of the untreated eye, was plotted against the CCC of the untreated eye, a correlation coefficient of 0.795 was obtained. The apparent and percentage reductions in CCC were also related by linear regression to the number of laser shots required, by correlation coefficients of 0.743 and 0.741, respectively.

The results show that the photothrombotic procedure does not produce corneal edema or polymorphonuclear leukocyte infiltration as has been found in previous studies employing laser induced photocoagulation. Thus, the formation of additional neovascularization and lipid deposition is avoided. Vascular occlusion by photothrombosis, effected with 8.5 times less incident intensity and 27.5 times less total light exposure than with photocoagulation, yielded an average reduction of corneal cholesterol content of 36% as opposed to an increase of 24% found with previous argon laser photocoagulation.

EXAMPLE 7

The histopathological and hemodynamic consequences of photochemically induced middle cerebral artery (MCA) thrombosis and recanalization were examined in the rat.

1. Methods and Materials

Normally fed male Sprague-Dawley rats weighting 280–330 gm were used. Anesthesia was induced with 4% halothane and maintained with 1.5% halothane, 70% $N_2O$ and a balance of $O_2$ delivered through a closely fitting face mask. Polyethylene catheters were inserted retrogradely into the right external carotid artery and right femoral artery and vein. The partial pressures of $O_2$ and $CO_2$ and the arterial pH were measured frequently. Rectal temperature was maintained at 37° C. by means of a heating pad.

Photochemically Induced MCA Occlusion:

Rats were mounted on a stereotaxic frame and the right MCA was exposed by a modified subtemporal approach. A portion of the jaw was removed, and the masseter muscle was retracted downward to facilitate exposure of the MCA. The mandibular joint was kept intact so as not to disturb normal feeding. To produce MCA occlusion in these studies, a low power He-Ne laser operating in the $TEM^*_{01}$ (doughnut) mode at 0.8 mW and at a wavelength of 543.5 nm (PMS Electro-Optics, Boulder, CO.) was used. The efficiency of this laser in interacting with rose bengal dye is appreciable (58%) in that its emission wavelength is near the absorption maximum of rose bengal in tissue (562 nm). The animal was moutned in a stereotaxic frame, and its right side was tilted upward by 35° in order for the laser beam to strike the proximal MCA tangentially. The ring-shaped beam was focused transversely onto the exposed MCA by two crossed cylindrical lenses of 1- and 2-inch focal length. The resulting focused spot, rectangular in shape, was ~200 μm wide (spanning the diameter of the MCA perpendicular to its axis) and 40 μm high (parallel to the MCA axis).

MCA thrombosis was induced in two steps. First, the linear beam was focused transversely on the MCA segment just distal to the rhinal branch. The intensity of laser irradiation at the focal site was 10 $W/cm^2$. Rose bengal was then injected intravenously (30 mg/ml in saline, 0.67 ml/kg bw weight). An orange fluorescence was immediately observed in the irradiated MCA segment, and a white thrombus began to form within the fluorescent segment and gradually elongated rostrally. Within 10 minutes, the MCA was completely occluded by a white thrombus the length of which was about two times the diameter of the MCA (~400 μm). Complete MCA occlusion was confirmed by inspection of the vessel during the injection of a 100-μl saline bolus through the retrograde external carotid catheter. Next, the laser beam was moved to the horizontal portion of the MCA, distal to the olfactory tract and proximal to the rhinal branch. A second thrombus was then induced at the site following an additional injection of the same dose of rose bengal. By the end of the second irradiation, a thrombus about 1.2 mm in length was present in the MCA, centered at the olfactory tract.

The invention having been described, it will be appreciated by those skilled in the art, that various modifications can be made within the scope of the following claims.

What is claimed is:

1. A method for the permanent occlusion of arteries having a diameter of at least 21 μm, which comprises the infusion of rose bengal dye into the bloodstream and irradiation of an individual artery with a laser light beam at a wavelength sufficient to electronically excite the rose bengal molecules, the laser light beam being focussed so as to maximize the overlap of its cross-sectional intensity profile with the distribution off photosensitizer dye bound to arterial endothelium, so that rose bengal dye absorbed to the luminal surface of the artery absorbs the light, thereby initiating a photochemical reaction resulting in photochemical injury to the vascular endothelium of the artery at the point of interaction of the rose bengal dye and the laser light light beam.

2. The method of claim 1, wherein the concentration of the rose bengal dye in blood is in an amount sufficient to induce photochemical injury to the vascular endothelium at the point of interaction of the rose bengal dye with the light beam.

3. The method of claim 2, wherein the initial concentration of the rose bengal dye in blood does not exceed about 680 μM.

4. The method of claim 1, wherein the laser light beam is an argon laser beam of an argon ion laser.

5. The method of claim 4, wherein the argon ion laser is operated at a wavelength range sufficient to electronically excite the rose bengal molecules, thereby initiating the photochemical process.

6. The method of claim 5, wherein the argon ion laser is operated at a wavelength of 514.5 nm.

7. The method of claim 1, wherein the laser light beam is an argon laser beam and the concentration of the rose bengal dye in blood is in the range of about 130 μM to about 680 μM.

8. The method of claim 1, wherein the laser light beam is a helium-neon laser beam of a helium-neon laser.

9. The method of claim 8, wherein the helium-neon laser is operated at a wavelength range sufficient to electronically excite the rose bengal molecules, thereby initiating the photochemical process.

10. The method of claim 9, wherein the helium-neon laser is operated at a wavelength of 543.5 nm.

11. The method of claim 1, wherein the laser light beam is a helium-neon laser beam and the concentration of the rose bengal dye in blood is in the range of about 340 μM to about 680 μM.

12. The method of claim 1, wherein the laser light beam is a dye laser beam of an argon-pumped dye laser.

13. The method of claim 12, wherein the argon-pumped dye laser is operated at a wavelength range sufficient to electronically excite the rose bengal molecules, thereby initiating the photochemical process.

14. The method of claim 13, wherein the argon-pumped dye laser is operated at the optimal wavelength of 562 nm.

15. The method of claim 1, wherein the laser light beam is a dye laser beam of an argon-pumped dye laser and the concentration of the rose bengal in blood is in the range of about 45 µM to about 230 µM.

16. The method of claim 1, wherein the laser light beam is a gaussian laser beam and the beam waist of the gaussian laser light beam overlaps the arterial diameter by 6% on either side.

17. A method for the permanent occlusion of arteries having a diameter of at least 21 µm, which comprises the infursion of erythrosin B dye into the blood stream and irradiation of an individual artery with a laser light beam at a wavelength sufficient to electronically excite the erythrosin B molecules, the laser light beam being focussed so as to maximize the overlap of its cross-sectional intensity profile with the distribution of photosensitizer dye bound to arterial endothelium, so that erythrosin B dye absorbed to the luminal surface of the artery absorbs the light, thereby initiating a photochemical reaction resulting in photochemical injury to the vascular endothelium of the artery at the point of interaction of the erythrosin B dye and the laser light beam.

18. The method of claim 17, wherein the concentration of the erythrosin B dye in blood is in an amount sufficient to induce photochemical injury to the vascular endothelium at the point of interaction of the erythrosin B dye with the light beam.

19. The method of claim 14, wherein the laser light beam is an argon laser beam of an argon ion laser.

20. The method of claim 19, wherein the argon ion laser is operated at a wavelength range sufficient to electronically excite the erythrosin B molecules, thereby initiating the photochemical process.

21. The method of claim 20, wherein the argon ion laser is operated at a wavelength of 528.7 nm.

22. The method of claim 20, wherein the argon ion laser is operated at a wavelength of 514.5 nm.

23. The method of claim 17, wherein the laser light beam is a gaussian laser beam and the beam waist of the gaussian laser beam overlaps the arterial diameter by 6% on either side.

* * * * *